United States Patent
Goodacre

(12) 
(10) Patent No.: US 6,887,885 B2
(45) Date of Patent: May 3, 2005

(54) IMIDAZO[4,5-C]PYRIDIN-4-ONE ANALOGUES AS GABA$_A$ RECEPTOR LIGANDS

(75) Inventor: Simon Charles Goodacre, Benington (GB)

(73) Assignee: Merck Sharp & Dohme Ltd, Hoddesdon (*) Notice: Subject to any disclaimer, the term of this patent is extended or adjusted under 35 U.S.C. 154(b) by 0 days.

(21) Appl. No.: 10/697,210

(22) Filed: Oct. 30, 2003

(65) Prior Publication Data

US 2004/0132767 A1 Jul. 8, 2004

(30) Foreign Application Priority Data

Oct. 31, 2002 (GB) ............................................. 0225399

(51) Int. Cl.$^7$ .................. A61K 31/437; A61K 31/4745; C07D 471/04; A61P 25/22
(52) U.S. Cl. ............. 514/303; 514/252.04; 514/255.05; 514/256; 546/118; 544/238; 544/398; 544/322; 544/333; 544/405
(58) Field of Search .......................... 546/118; 514/303

(56) References Cited

FOREIGN PATENT DOCUMENTS

WO          WO 00/40583      *   7/2000

* cited by examiner

*Primary Examiner*—Evelyn Mei Huang
(74) *Attorney, Agent, or Firm*—J. Eric Thies; Melvin Winokur

(57) ABSTRACT

A compound of formula I, or a pharmaceutically acceptable salt thereof:

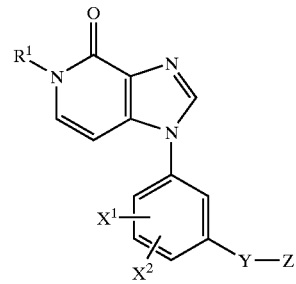

wherein $X^1$ represents hydrogen, halogen, $C_{1-6}$ alkyl, trifluoromethyl or $C_{1-6}$ alkoxy;

$X^2$ represents hydrogen or halogen;

Y represents a chemical bond, an oxygen atom, or a —NH— linkage;

Z represents an optionally substituted aryl or heteroaryl group;

$R^1$ represents hydrocarbon, a heterocyclic group, trifluoromethyl, —SO$_2$R$^a$, —SO$_2$NR$^a$R$^b$, —COR$^a$, —CO$_2$R$^a$ or —CONR$^a$R$^b$; and $R^a$ and $R^b$ independently represent hydrogen, hydrocarbon or a heterocyclic group;

pharmaceutical compositions including the compound and methods for treating anxiety, convulsions and cognitive disorders are disclosed.

9 Claims, No Drawings

IMIDAZO[4,5-C]PYRIDIN-4-ONE ANALOGUES AS GABA$_A$ RECEPTOR LIGANDS

CROSS REFERENCE TO RELATED APPLICATIONS

This application claims priority under 35 U.S.C. §119 from GB Application No. 0225399.5 filed Oct. 31, 2002.

The present invention relates to a class of substituted imidazo-pyridinone derivatives and to their use in therapy. More particularly, this invention is concerned with imidazo [4,5-c]pyridin-4-one analogues which are substituted in the 1-position by a substituted phenyl ring. These compounds are ligands for GABA$_A$ receptors and are therefore useful in the therapy of adverse neurological disorders.

Receptors for the major inhibitory neurotransmitter, gamma-aminobutyric acid (GABA), are divided into two main classes: (1) GABA$_A$ receptors, which are members of the ligand-gated ion channel superfamily; and (2) GABA$_B$ receptors, which may be members of the G-protein linked receptor superfamily. Since the first cDNAs encoding individual GABA$_A$ receptor subunits were cloned the number of known members of the mammalian family has grown to include at least six $\alpha$ subunits, four $\beta$ subunits, three $\gamma$ subunits, one $\delta$ subunit, one $\epsilon$ subunit and two $\rho$ subunits.

Although knowledge of the diversity of the GABA$_A$ receptor gene family represents a huge step forward in our understanding of this ligand-gated ion channel, insight into the extent of subtype diversity is still at an early stage. It has been indicated that an $\alpha$ subunit, a $\beta$ subunit and a $\gamma$ subunit constitute the minimum requirement for forming a fully functional GABA$_A$ receptor expressed by transiently transfecting cDNAs into cells. As indicated above, $\delta$, $\epsilon$ and $\rho$ subunits also exist, but are present only to a minor extent in GABA$_A$ receptor populations.

Studies of receptor size and visualisation by electron microscopy conclude that, like other members of the ligand-gated ion channel family, the native GABA$_A$ receptor exists in pentameric form. The selection of at least one $\alpha$, one $\beta$ and one $\gamma$ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, $\alpha1\beta2\gamma2$, $\alpha2\beta\gamma1$, $\alpha2\beta2/3\gamma2$, $\alpha3\beta\gamma2/3$, $\alpha4\beta\delta$, $\alpha5\beta3\gamma2/3$, $\alpha6\beta\gamma2$ and $\alpha6\beta\delta$. Subtype assemblies containing an $\alpha1$ subunit are present in most areas of the brain and are thought to account for over 40% of GABA$_A$ receptors in the rat. Subtype assemblies containing $\alpha2$ and $\alpha3$ subunits respectively are thought to account for about 25% and 17% of GABA$_A$ receptors in the rat. Subtype assemblies containing an $\alpha5$ subunit are expressed predominantly in the hippocampus and cortex and are thought to represent about 4% of GABA$_A$ receptors in the rat.

A characteristic property of all known GABA$_A$ receptors is the presence of a number of modulatory sites, one of which is the benzodiazepine (BZ) binding site. The BZ binding site is the most explored of the GABA$_A$ receptor modulatory sites, and is the site through which anxiolytic drugs such as diazepam and temazepam exert their effect. Before the cloning of the GABA$_A$ receptor gene family, the benzodiazepine binding site was historically subdivided into two subtypes, BZ1 and BZ2, on the basis of radioligand binding studies. The BZ1 subtype has been shown to be pharmacologically equivalent to a GABA$_A$ receptor comprising the $\alpha1$ subunit in combination with a $\beta$ subunit and $\gamma2$. This is the most abundant GABA$_A$ receptor subtype, and is believed to represent almost half of all GABA$_A$ receptors in the brain.

Two other major populations are the $\alpha2\beta\gamma2$ and $\alpha3\beta\gamma2/3$ subtypes. Together these constitute approximately a further 35% of the total GABA$_A$ receptor repertoire. Pharmacologically this combination appears to be equivalent to the BZ2 subtype as defined previously by radioligand binding, although the BZ2 subtype may also include certain $\alpha5$-containing subtype assemblies. The physiological role of these subtypes has hitherto been unclear because no sufficiently selective agonists or antagonists were known.

It is now believed that agents acting as BZ agonists at $\alpha1\beta\gamma2$, $\alpha2\beta\gamma2$ or $\alpha3\beta\gamma2$ subtypes will possess desirable anxiolytic properties. Compounds which are modulators of the benzodiazepine binding site of the GABA$_A$ receptor by acting as BZ agonists are referred to hereinafter as "GABA$_A$ receptor agonists". The $\alpha1$-selective GABA$_A$ receptor agonists alpidem and zolpidem are clinically prescribed as hypnotic agents, suggesting that at least some of the sedation associated with known anxiolytic drugs which act at the BZ1 binding site is mediated through GABA$_A$ receptors containing the $\alpha1$ subunit. Accordingly, it is considered that GABA$_A$ receptor agonists which interact more favourably with the $\alpha2$ and/or $\alpha3$ subunit than with $\alpha1$ will be effective in the treatment of anxiety with a reduced propensity to cause sedation. Moreover, agents which are inverse agonists of the $\alpha5$ subunit are likely to be beneficial in enhancing cognition, for example in subjects suffering from dementing conditions such as Alzheimer's disease. Also, agents which are antagonists or inverse agonists at $\alpha1$ might be employed to reverse sedation or hypnosis caused by $\alpha1$ agonists.

The compounds of the present invention, being selective ligands for GABA$_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; Tourette's syndrome; speech disorders, including stuttering; and disorders of circadian rhythm, e.g. in subjects suffering from the effects of jet lag or shift work.

Further disorders for which selective ligands for GABA$_A$ receptors may be of benefit include pain and nociception; emesis, including acute, delayed and anticipatory emesis, in particular emesis induced by chemotherapy or radiation, as well as motion sickness, and post-operative nausea and vomiting; eating disorders including anorexia nervosa and bulimia nervosa; premenstrual syndrome; muscle spasm or spasticity, e.g. in paraplegic patients; hearing disorders, including tinnitus and age-related hearing impairment; urinary incontinence; and the effects of substance abuse or dependency, including alcohol withdrawal. Selective ligands for GABA$_A$ receptors may be beneficial in enhancing cognition, for example in subjects suffering from dementing conditions such as Alzheimer's disease; and may also be effective as pre-medication prior to anaesthesia or minor procedures such as endoscopy, including gastric endoscopy.

In addition, the compounds in accordance with the present invention may be useful as radioligands in assays for detecting compounds capable of binding to the human $GABA_A$ receptor.

The present invention provides a class of imidazopyridinone derivatives which possess desirable binding properties at various $GABA_A$ receptor subtypes. The compounds in accordance with the present invention have good affinity as ligands for the α2 and/or α3 and/or α5 subunit of the human $GABA_A$ receptor. The compounds of this invention may interact more favourably with the α2 and/or α3 subunit than with the α1 subunit; and/or may interact more favourably with the α5 subunit than with the α1 subunit.

The compounds of the present invention are $GABA_A$ receptor subtype ligands having a binding affinity ($K_i$) for the α2 and/or α3 and/or α5 subunit, as measured in the assay described hereinbelow, of 200 nM or less, typically of 100 nM or less, and ideally of 20 nM or less. The compounds in accordance with this invention may possess at least a 2-fold, suitably at least a 5-fold, and advantageously at least a 10-fold, selective affinity for the α2 and/or α3 and/or α5 subunit relative to the α1 subunit. However, compounds which are not selective in terms of their binding affinity for the α2 and/or α3 and/or α5 subunit relative to the α1 subunit are also encompassed within the scope of the present invention; such compounds will desirably exhibit functional selectivity in terms of zero or weak (positive or negative) efficacy at the α1 subunit and (i) a full or partial agonist profile at the α2 and/or α3 subunit, and/or (ii) an inverse agonist profile at the α5 subunit.

The present invention provides a compound of formula I, or a pharmaceutically acceptable salt thereof:

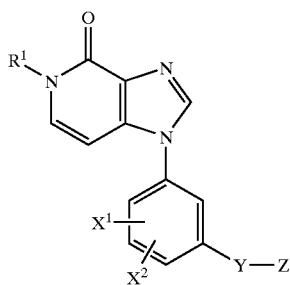

(I)

wherein $X^1$ represents hydrogen, halogen, $C_{1-6}$ alkyl, trifluoromethyl or $C_{1-6}$ alkoxy;

$X^2$ represents hydrogen or halogen;

Y represents a chemical bond, an oxygen atom, or a —NH— linkage;

Z represents an optionally substituted aryl or heteroaryl group;

$R^1$ represents hydrocarbon, a heterocyclic group, trifluoromethyl, —$SO_2R^a$, —$SO_2NR^aR^b$, —$COR^a$, —$CO_2R^a$ or —$CONR^aR^b$; and $R^a$ and $R^b$ independently represent hydrogen, hydrocarbon or a heterocyclic group.

The aryl or heteroaryl group Z in the compounds of formula I above may be unsubstituted, or substituted by one or more substituents. Typically, the group Z will be unsubstituted, or substituted by one or two substituents. Suitably, the group Z is unsubstituted or monosubstituted. Typical substituents on the group Z include halogen, cyano, nitro, $C_{1-6}$ alkyl, hydroxy, $C_{1-6}$ alkoxy, oxy, $C_{1-6}$ alkylsulphonyl, amino, aminocarbonyl, formyl, $C_{2-6}$ alkoxycarbonyl and —$CR^a$=$NOR^b$, wherein $R^a$ and $R^b$ are as defined above.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, indanyl, aryl and aryl($C_{1-6}$)alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl and heteroaryl($C_{1-6}$)alkyl groups.

Suitable alkyl groups include straight-chained and branched alkyl groups containing from 1 to 6 carbon atoms. Typical examples include methyl and ethyl groups, and straight-chained or branched propyl, butyl and pentyl groups. Particular alkyl groups are methyl, ethyl, n-propyl, isopropyl, isobutyl, tert-butyl and 2,2-dimethylpropyl. Derived expressions such as "$C_{1-6}$ alkoxy", "$C_{1-6}$ alkylamino" and "$C_{1-6}$ alkylsulphonyl" are to be construed accordingly.

Suitable alkenyl groups include straight-chained and branched alkenyl groups containing from 2 to 6 carbon atoms. Typical examples include vinyl, allyl and dimethylallyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Typical examples of $C_{3-7}$ cycloalkyl($C_{1-6}$)alkyl groups include cyclopropylmethyl, cyclohexylmethyl and cyclohexylethyl.

Particular indanyl groups include indan-1-yl and indan-2-yl.

Particular aryl groups include phenyl and naphthyl, preferably phenyl.

Particular aryl($C_{1-16}$)alkyl groups include benzyl, phenylethyl, phenylpropyl and naphthylmethyl.

Suitable heterocycloalkyl groups include azetidinyl, pyrrolidinyl, piperidinyl, piperazinyl, morpholinyl and thiomorpholinyl groups.

Suitable heteroaryl groups include pyridinyl, quinolinyl, isoquinolinyl, pyridazinyl, pyrimidinyl, pyrazinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyrazinylmethyl, quinolinylmethyl and isoquinolinylmethyl.

The hydrocarbon and heterocyclic groups may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, aminocarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, —$NR^VR^W$, —$NR^VCOR^W$, —$NR^VCO_2R^W$, —$NR^VSO_2R^W$, —$CH_2NR^VSO_2R^W$, —$NHCONR^VR^W$, —$CONR^VR^W$, —$SO_2NR^VR^W$ and —$CH_2SO_2NR^VR^W$, in which $R^V$ and $R^W$ independently represent hydrogen, $C_{1-6}$ alkyl, aryl or aryl($C_{1-6}$)alkyl.

The term "halogen" as used herein includes fluorine, chlorine, bromine and iodine, especially fluoro or chloro.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Suitable values for the $X^1$ substituent include hydrogen, fluoro, chloro, methyl, trifluoromethyl and methoxy; in particular hydrogen or fluoro; and especially fluoro.

Typical values of $X^2$ include hydrogen and fluoro, especially hydrogen.

In a preferred embodiment, Y represents a chemical bond. In another embodiment, Y represents an oxygen atom. In a further embodiment, Y represents a —NH—linkage.

Selected values for the substituent Z include phenyl, pyridinyl, pyridazinyl, pyrimidinyl, pyrazinyl, furyl, thienyl, oxazolyl, isoxazolyl, thiazolyl, isothiazolyl, pyrrolyl, pyrazolyl, imidazolyl, oxadiazolyl, thiadiazolyl, triazolyl and tetrazolyl, any of which groups may be optionally substituted by one or more substituents.

In one favoured embodiment, Z represents an optionally substituted phenyl group, in particular monosubstituted or disubstituted phenyl. In another favoured embodiment, Z represents optionally substituted pyridinyl, especially unsubstituted, monosubstituted or disubstituted pyridin-2-yl, pyridin-3-yl or pyridin-4-yl.

Examples of suitable substituents on the group Z include fluoro, chloro, cyano, nitro, methyl, hydroxy, methoxy, oxy, methanesulphonyl, amino, aminocarbonyl, formyl, methoxycarbonyl and —CH=NOH.

Examples of particular substituents on the group Z include fluoro and cyano.

Detailed values of Z include difluorophenyl, cyanophenyl, (cyano)(fluoro)phenyl, (chloro)(cyano) phenyl, nitrophenyl, methoxyphenyl, methanesulphonylphenyl, pyridinyl, fluoro-pyridinyl, difluoro-pyridinyl, (amino)(chloro)pyridinyl, cyano-pyridinyl, methyl-pyridinyl, hydroxy-pyridinyl, methoxy-pyridinyl, oxy-pyridinyl, aminocarbonyl-pyridinyl, pyridazinyl, pyrimidinyl, pyrazinyl, cyano-thienyl, aminocarbonyl-thienyl, formyl-thienyl, methoxycarbonyl-thienyl, thienyl-CH=NOH, thiazolyl, isothiazolyl, pyrrolyl, pyrazolyl, imidazolyl, triazolyl and methyl-tetrazolyl.

Specific values of Z include difluorophenyl, cyanophenyl, (cyano)(fluoro)phenyl, pyridinyl and fluoro-pyridinyl.

In one embodiment, Z represents (cyano)(fluoro)phenyl, especially 2-cyano-5-fluorophenyl.

Typically, $R^1$ represents hydrocarbon, a heterocyclic group, trifluoromethyl, —$COR^a$ or —$CO_2R^a$.

Typical values of $R^a$ include hydrogen and $C_{1-6}$ alkyl. Suitably, $R^a$ represents hydrogen or methyl.

Typical values of $R^b$ include hydrogen, $C_{1-6}$ alkyl, hydroxy($C_{1-6}$)alkyl and di($C_{1-6}$)alkylamino($C_{1-6}$)alkyl. Suitably, $R^b$ represents hydrogen, methyl, ethyl, hydroxyethyl or dimethylaminoethyl. Particular values of $R^b$ include hydrogen, hydroxyethyl and dimethylaminoethyl, especially hydrogen or dimethylaminoethyl.

Suitable values of $R^1$ include $C_{1-6}$ alkyl, halo($C_{1-6}$)alkyl, dihalo($C_{1-6}$)alkyl, hydroxy($C_{1-6}$)alkyl, dihydroxy($C_{1-6}$) alkyl, $C_{1-6}$ alkoxy($C_{1-6}$)alkyl, di($C_{1-6}$)alkoxy($C_{1-6}$)alkyl, cyano($C_{1-6}$)alkyl, $C_{2-6}$ alkoxycarbonyl($C_{1-6}$)alkyl, $C_{3-7}$ cycloalkyl, heteroaryl, $C_{1-6}$ alkyl-heteroaryl, heteroaryl($C_{1-6}$)alkyl, trifluoromethyl, formyl, $C_{2-6}$ alkylcarbonyl and $C_{2-6}$ alkoxycarbonyl.

Representative values of $R^1$ include $C_{1-6}$ alkyl, halo($C_{1-6}$)alkyl, hydroxy($C_{1-6}$)alkyl and trifluoromethyl.

Individual values of $R^1$ include methyl, fluoromethyl, difluoromethyl, hydroxymethyl, methoxymethyl, dimethoxymethyl, hydroxyethyl (especially 1-hydroxyethyl), fluoroethyl (especially 1-fluoroethyl), difluoroethyl (especially 1,1-difluoroethyl), dimethoxyethyl (especially 1,1-dimethoxyethyl), isopropyl, hydroxypropyl (especially 2-hydroxyprop-2-yl), dihydroxypropyl (especially 1,2-dihydroxyprop-2-yl), fluoropropyl (especially 2-fluoroprop-2-yl), cyanopropyl (especially 2-cyanoprop-2-yl), methoxycarbonylpropyl (especially 2-methoxycarbonylprop-2-yl), tert-butyl, hydroxybutyl (especially 1-hydroxy-2-methylprop-2-yl), cyclopropyl, pyridinyl, furyl, thienyl, oxazolyl, methylthiazolyl, methyloxadiazolyl, imidazolylmethyl, triazolylmethyl, trifluoromethyl, formyl, acetyl and methoxycarbonyl.

In a favoured embodiment, $R^1$ represents 2-hydroxyprop-2-yl. In another embodiment, $R^1$ represents 2-fluoroprop-2-yl. In an additional embodiment, $R^1$ represents trifluoromethyl. In a further embodiment, $R^1$ represents methyl.

A particular sub-class of compounds according to the invention is represented by the compounds of formula IIA, and pharmaceutically acceptable salts thereof:

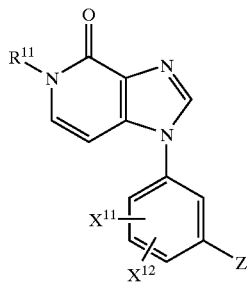

(IIA)

wherein

Z is as defined above;

$X^{11}$ represents hydrogen, fluoro, chloro, methyl, trifluoromethyl or methoxy;

$X^{12}$ represents hydrogen or fluoro; and $R^{11}$ represents $C_{1-6}$ alkyl, halo($C_{1-6}$)alkyl, dihalo($C_{1-6}$)alkyl, hydroxy($C_{1-6}$)alkyl, dihydroxy($C_{1-6}$)alkyl, $C_{1-6}$ alkoxy($C_{1-6}$)alkyl, di($C_{1-6}$)alkoxy($C_{1-6}$)alkyl, cyano($C_{1-6}$) alkyl, $C_{2-6}$ alkoxycarbonyl($C_{1-6}$)alkyl, $C_{3-7}$ cycloalkyl, heteroaryl, $C_{1-6}$ alkyl-heteroaryl, heteroaryl($C_{1-16}$)alkyl, trifluoromethyl, formyl, $C_{2-6}$ alkylcarbonyl or $C_{2-6}$ alkoxycarbonyl.

Suitable values of $X^{11}$ include hydrogen and fluoro, especially fluoro.

In a favoured embodiment, $X^{12}$ represents hydrogen. In another embodiment, $X^{12}$ represents fluoro.

Where $R^{11}$ represents heteroaryl, this group is suitably pyridinyl, furyl, thienyl or oxazolyl.

Where $R^{11}$ represents $C_{1-6}$ alkyl-heteroaryl, this group is suitably methylthiazolyl (e.g. 2-methylthiazol-5-yl) or methyloxadiazolyl (e.g. 3-methyl-[1,2,4]oxadiazol-5-yl).

Where $R^{11}$ represents heteroaryl($C_{1-6}$)alkyl, this group is suitably imidazolylmethyl or triazolylmethyl.

Representative values of $R^{11}$ include $C_{1-6}$ alkyl, hydroxy($C_{1-6}$)alkyl, fluoro($C_{1-6}$)alkyl and trifluoromethyl.

Individual values of $R^{11}$ include methyl, fluoromethyl, difluoromethyl, hydroxymethyl, methoxymethyl, dimethoxymethyl, hydroxyethyl (especially 1-hydroxyethyl), fluoroethyl (especially 1-fluoroethyl), difluoroethyl (especially 1,1-difluoroethyl), dimethoxyethyl (especially 1,1-dimethoxyethyl), isopropyl, hydroxypropyl (especially 2-hydroxyprop-2-yl), dihydroxypropyl (especially 1,2-dihydroxyprop-2-yl), fluoropropyl (especially 2-fluoroprop-2-yl), cyanopropyl (especially 2-cyanoprop-2-yl), methoxycarbonylpropyl (especially 2-methoxycarbonylprop-2-yl), tert-butyl, hydroxybutyl (especially 1-hydroxy-2-methylprop-2-yl), cyclopropyl, pyridinyl, furyl, thienyl, oxazolyl, methylthiazolyl, methyloxadiazolyl, imidazolylmethyl, triazolylmethyl, trifluoromethyl, formyl, acetyl and methoxycarbonyl.

In a favoured embodiment, $R^{11}$ represents 2-hydroxyprop-2-yl. In another embodiment, $R^{11}$ represents 2-fluoroprop-2-yl. In an additional embodiment, $R^{11}$ represents trifluoromethyl. In a further embodiment, $R^{11}$ represents methyl.

One representative subset of the compounds of formula IIA above is represented by the compounds of formula IIB, and pharmaceutically acceptable salts thereof:

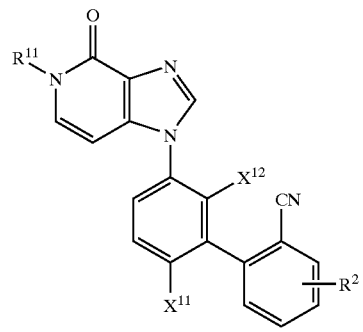

(IIB)

wherein $X^{11}$, $X^{12}$ and $R^{11}$ are as defined above; and $R^2$ represents hydrogen or fluoro.

In one embodiment, $R^2$ is hydrogen.

In another embodiment, $R^2$ is fluoro, in which case the fluorine atom $R^2$ is favourably attached to the phenyl ring at the 4-, 5- or 6-position (relative to the cyano group at position 2).

Another representative subset of the compounds of formula IIA above is represented by the compounds of formula IIC, and pharmaceutically acceptable salts thereof:

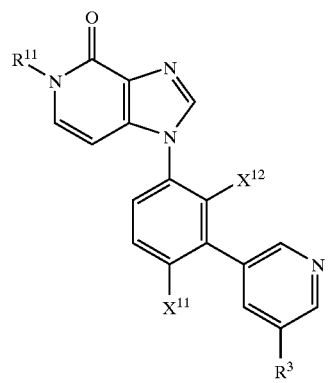

(IIC)

wherein $X^{11}$, $X^{12}$ and $R^{11}$ are as defined above; and $R^3$ represents hydrogen or fluoro.

In one embodiment, $R^3$ is hydrogen.

In another embodiment, $R^3$ is fluoro.

A further representative subset of the compounds of formula IIA above is represented by the compounds of formula IID, and pharmaceutically acceptable salts thereof:

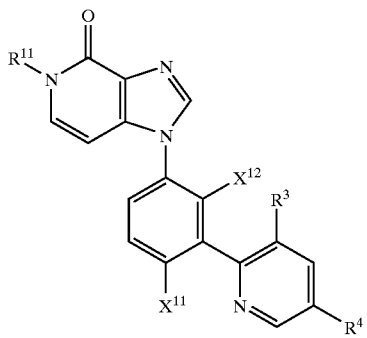

(IID)

wherein $X^{11}$, $X^{12}$, $R^3$ and $R^{11}$ are as defined above; and

R⁴ represents hydrogen or fluoro.

Suitably, R⁴ represents hydrogen.

In another embodiment, R⁴ represents fluoro.

Specific compounds within the scope of the present invention include:

3'-(5-methyl-4-oxo-4,5-dihydroimidazo[4,5-c]pyridin-1-yl)biphenyl-2-carbonitrile;

1-[4-fluoro-3-(5-fluoropyridin-3-yl)phenyl]-5-methyl-1,5-dihydroimidazo[4,5-c]pyridin-4-one;

5,2'-difluoro-5'-(5-methyl-4-oxo-4,5-dihydroimidazo[4,5-c]pyridin-1-yl)-biphenyl-2-carbonitrile;

1-[4-fluoro-3-(pyridin-3-yl)phenyl]-5-methyl-1,5-dihydroimidazo[4,5-c]pyridin-4-one;

5-methyl-1-(2,2',3'-trifluorobiphenyl-5-yl)-1,5-dihydroimidazo[4,5-c]pyridin-4-one;

4,2'-difluoro-5'-(5-methyl-4-oxo-4,5-dihydroimidazo[4,5-c]pyridin-1-yl)biphenyl-2-carbonitrile;

and pharmaceutically acceptable salts thereof.

Also provided by the present invention is a method for the treatment and/or prevention of anxiety which comprises administering to a patient in need of such treatment an effective amount of a compound of formula I as defined above or a pharmaceutically acceptable salt thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof.

The binding affinity ($K_i$) of the compounds according to the present invention for the α3 subunit of the human $GABA_A$ receptor is conveniently as measured in the assay described hereinbelow. The α3 subunit binding affinity ($K_i$) of the anxiolytic compounds of the invention is ideally 50 nM or less, preferably 10 nM or less, and more preferably 5 nM or less.

The anxiolytic compounds according to the present invention will ideally elicit at least a 40%, preferably at least a 50%, and more preferably at least a 60%, potentiation of the GABA $EC_{20}$ response in stably transfected recombinant cell lines expressing the α3 subunit of the human $GABA_A$ receptor. Moreover, the compounds of the invention will ideally elicit at most a 30%, preferably at most a 20%, and more preferably at most a 10%, potentiation of the GABA $EC_{20}$ response in stably transfected recombinant cell lines expressing the α1 subunit of the human $GABA_A$ receptor.

The potentiation of the GABA $EC_{20}$ response in stably transfected cell lines expressing the α3 and α1 subunits of the human $GABA_A$ receptor can conveniently be measured by procedures analogous to the protocol described in Wafford et al., *Mol. Pharmacol.*, 1996, 50, 670–678. The procedure will suitably be carried out utilising cultures of stably transfected eukaryotic cells, typically of stably transfected mouse Ltk fibroblast cells.

The compounds according to the present invention may exhibit anxiolytic activity, as may be demonstrated by a positive response in the elevated plus maze and conditioned suppression of drinking tests (cf. Dawson et al., *Psychopharmacology*, 1995, 121, 109–117). Moreover, the compounds of the invention are likely to be substantially non-sedating, as may be confirmed by an appropriate result obtained from the response sensitivity (chain-pulling) test (cf. Bayley et al., *J. Psychopharmacol.*, 1996, 10, 206–213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492–501.

In another aspect, the present invention provides a method for the treatment and/or prevention of cognitive disorders, including dementing conditions such as Alzheimer's disease, which comprises administering to a patient in need of such treatment an effective amount of a compound of formula I as defined above or a pharmaceutically acceptable salt thereof.

Cognition enhancement can be shown by testing the compounds in the Morris watermaze as reported by McNamara and Skelton, *Psychobiology*, 1993, 21, 101–108. Further details of relevant methodology are described in WO 96/25948.

Cognitive disorders for which the compounds of the present invention may be of benefit include delirium, dementia, amnestic disorders, and cognition deficits, including age-related memory deficits, due to traumatic injury, stroke, Parkinson's disease and Down Syndrome. Any of these conditions may be attributable to substance abuse or withdrawal. Examples of dementia include dementia of the Alzheimer's type with early or late onset, and vascular dementia, any of which may be uncomplicated or accompanied by delirium, delusions or depressed mood; and dementia due to HIV disease, head trauma, Parkinson's disease or Creutzfeld-Jakob disease.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former.

The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of neurological disorders, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises reacting a compound of formula III:

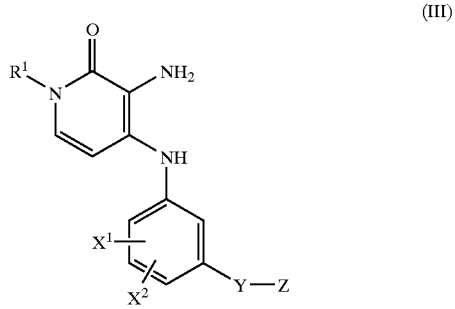

(III)

wherein $X^1$, $X^2$, Y, Z and $R^1$ are as defined above; with formic acid.

The reaction is conveniently accomplished by stirring the reactants at an elevated temperature, typically in the region of 95° C.

The intermediates of formula III may be prepared by reduction of a compound of formula IV:

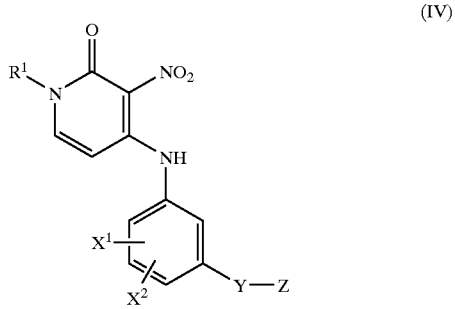

(IV)

wherein $X^1$, $X^2$, Y, Z and $R^1$ are as defined above.

The reduction is conveniently effected by treating compound IV with hydrogen in the presence of a hydrogenation catalyst, e.g. platinum oxide, in a suitable solvent, for example a mixture of ethanol and ethyl acetate.

The intermediates of formula IV may be prepared by reacting a compound of formula V with a compound of formula VI:

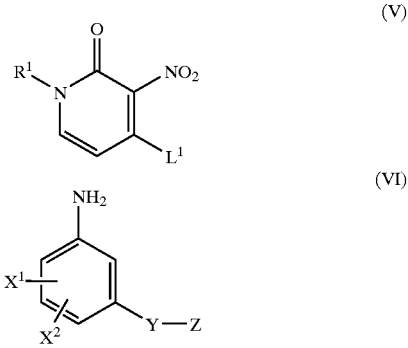

(V)

(VI)

wherein $X^1$, $X^2$, Y, Z and $R^1$ are as defined above, and $L^1$ represents a suitable leaving group.

The leaving group $L^1$ is typically a halogen atom, e.g. chloro.

The reaction between compounds V and VI is conveniently effected by heating the reactants, to a temperature typically in the region of 90° C., in the presence of a base such as triethylamine, in a solvent such as dimethylsulfoxide.

In another procedure, the compounds according to the present invention in which Y represents a chemical bond may be prepared by a process which comprises reacting a compound of formula VII with a compound of formula VIII:

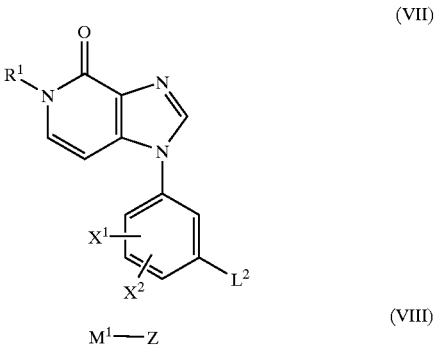

(VII)

(VIII)

wherein $X^1$, $X^2$, Z and $R^1$ are as defined above, $L^2$ represents a suitable leaving group, and $M^1$ represents a boronic acid moiety —$B(OH)_2$ or a cyclic ester thereof formed with an organic diol, e.g. pinacol, 1,3-propanediol or neopentyl glycol, or $M^1$ represents —$Sn(Alk)_3$ in which Alk represents a $C_{1-6}$ alkyl group, typically n-butyl; in the presence of a transition metal catalyst.

In the compounds of formula VII above, the leaving group $L^2$ is typically trifluoromethanesulfonyloxy (triflyloxy); or a halogen atom, e.g. bromo.

The transition metal catalyst of use in the reaction between compounds VII and VIII is suitably tetrakis (triphenylphosphine)-palladium(0). The reaction is conveniently carried out at an elevated temperature in a solvent such as N,N-dimethylacetamide, 1,2-dimethoxyethane, 1,4-dioxane or tetrahydrofuran, advantageously in the presence of potassium phosphate, copper(I) iodide, sodium carbonate or cesium carbonate. Alternatively, the transition metal catalyst employed may be tris(dibenzylideneacetone) dipalladium(0), in which case the reaction is conveniently effected at an elevated temperature in a solvent such as 1,4-dioxane, typically in the presence of tri-tert-butylphosphine and potassium phosphate.

Alternatively, the compounds according to the present invention in which Y represents a chemical bond may be prepared by a process which comprises reacting a compound of formula IX with a compound of formula X:

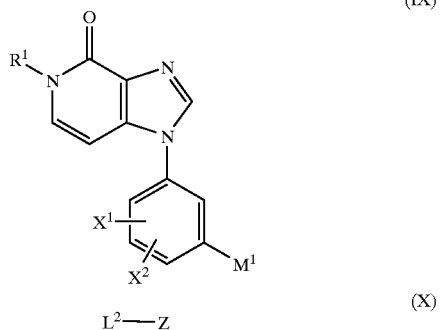

(IX)

(X)

wherein $X^1$, $X^2$, Z, $R^1$, $L^2$ and $M^1$ are as defined above; in the presence of a transition metal catalyst; under conditions analogous to those described above for the reaction between compounds VII and VIII.

In an additional procedure, the compounds according to the present invention in which Y represents an oxygen atom may be prepared by a process which comprises reacting a compound of formula X as defined above with a compound of formula XI:

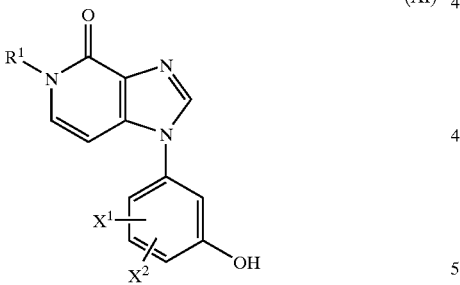

(XI)

wherein $X^1$, $X^2$ and $R^1$ are as defined above.

The reaction is conveniently carried out under basic conditions, e.g. using sodium hydride in a solvent such as N,N-dimethylformamide, typically at an elevated temperature which may be in the region of 120° C.

In a further procedure, the compounds according to the present invention in which Y represents a —NH— linkage may be prepared by a process which comprises reacting a compound of formula X as defined above with a compound of formula XII:

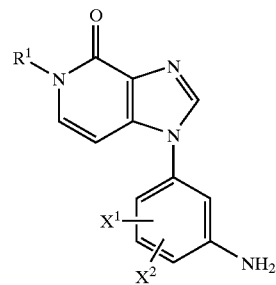

(XII)

wherein $X^1$, $X^2$ and $R^1$ are as defined above.

In relation to the reaction between compounds X and XII, the leaving group $L^2$ in the compounds of formula X may suitably represent fluoro.

The reaction between compounds X and XII is conveniently carried out by heating the reactants, typically at a temperature in the region of 120° C., in a solvent such as N,N-dimethylformamide.

Where $M^1$ in the intermediates of formula VIII and IX above represents a boronic acid moiety —B(OH)$_2$ or a cyclic ester thereof formed with pinacol or neopentyl glycol, the relevant compound VIII or IX may be prepared by reacting bis(pinacolato)diboron or bis(neopentyl glycolato) diborane respectively with a compound of formula X or VII as defined above; in the presence of a transition metal catalyst.

The transition metal catalyst of use in the reaction between bis(pinacolato)diboron or bis(neopentyl glycolato) diborane and compound X or VII is suitably dichloro[1,1'-bis(diphenylphosphino)ferrocene]-palladium(II). The reaction is conveniently carried out at an elevated temperature in a solvent such as 1,4-dioxane, optionally in admixture with dimethylsulfoxide, typically in the presence of 1,1'-bis(diphenylphosphino)ferrocene and/or potassium acetate.

The intermediates of formula VII above may be prepared by reacting a compound of formula XIII:

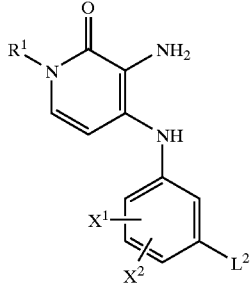

(XIII)

wherein $X^1$, $X^2$, $R^1$ and $L^2$ are as defined above; with formic acid; under conditions analogous to those described above for the reaction between compound III and formic acid.

The intermediates of formula XIII may be prepared by reaction of a compound of formula V as defined above with a compound of formula XIV:

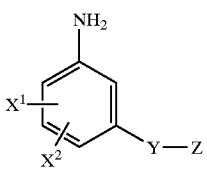

(XIV)

wherein $X^1$, $X^2$, Y and Z are as defined above; under conditions analogous to those described above for the reaction between compounds V and VI; followed by reduction of the nitro group in the resulting compound, under conditions analogous to those described above for the reduction of the nitro group in compound IV.

Where $L^2$ in the intermediates of formula VII above represents triflyloxy, the relevant compound VII may be prepared by reacting the appropriate compound of formula XI as defined above with triflic anhydride, typically in the presence of pyridine.

The intermediates of formula XI above may suitably be prepared from the appropriate methoxy-substituted precursor of formula XV:

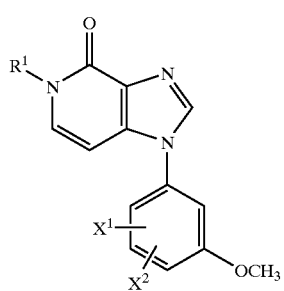

(XV)

wherein $X^1$, $X^2$ and $R^1$ are as defined above; by treatment with boron tribromide, typically in chloroform or dichloromethane; or with hydrogen bromide, typically in acetic acid at reflux.

The intermediates of formula XII and XV above may be prepared by reacting a compound of formula V as defined above with the appropriate compound of formula XVI:

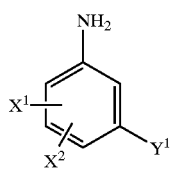

(XVI)

wherein $X^1$ and $X^2$ are as defined above, and $Y^1$ represents amino or methoxy; under conditions analogous to those described above for the reaction between compounds V and VI; followed by reduction of the nitro group in the resulting compound, under conditions analogous to those described above for the reduction of the nitro group in compound IV; followed by reaction of the product thereby obtained with formic acid, under conditions analogous to those described above for the reaction between compound III and formic acid.

The compounds according to the invention in which Y represents a chemical bond and Z represents pyrrol-1-yl may be prepared by reacting a compound of formula XII as defined above with 2,5-dimethoxy-tetrahydrofuran. The reaction is conveniently accomplished at an elevated temperature in a solvent such as acetic acid.

Where they are not commercially available, the starting materials of formula V, VI, X, XIV and XVI may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art. For example, a compound of formula I wherein $R^1$ represents —C(O-Alk$^1$)$_2$R$^a$ initially obtained, wherein Alk$^1$ is $C_{1-6}$ alkyl, typically methyl or ethyl, may be converted into the corresponding compound of formula I wherein $R^1$ represents —COR$^a$ by hydrolysis with a mineral acid, typically aqueous hydrochloric acid. A compound wherein $R^1$ represents formyl may be reduced with sodium triacetoxyborohydride to the corresponding compound wherein $R^1$ represents hydroxymethyl. A compound of formula I wherein $R^1$ represents $C_{2-6}$ alkoxycarbonyl may be reduced with lithium aluminium hydride to the corresponding compound of formula I wherein $R^1$ represents hydroxymethyl. A compound of formula I wherein $R^1$ represents hydroxymethyl may be oxidised to the corresponding compound of formula I wherein $R^1$ represents formyl by treatment with manganese dioxide. Alternatively, the compound of formula I wherein $R^1$ represents formyl may be reacted with a Grignard reagent of formula $R^a$MgBr to afford a compound of formula I wherein $R^1$ represents —CH(OH)R$^a$, and this compound may in turn be oxidised using manganese dioxide to the corresponding compound of formula I wherein $R^1$ represents —COR$^a$. A compound of formula I wherein $R^1$ represents —CH(OH)R$^a$ may be converted into the corresponding compound of formula I wherein $R^1$ represents —CHFR$^a$ by treatment with (diethylamino)sulfur trifluoride (DAST). Similarly, a compound of formula I wherein $R^1$ represents —COR$^a$ may be converted into the corresponding compound of formula I wherein $R^1$ represents —CF$_2$R$^a$ by treatment with DAST. A compound of formula I wherein $R^1$ represents —COCH$_3$ may be treated with thioacetamide in the presence of pyridinium tribromide to furnish the corresponding compound of formula I wherein $R^1$ represents 2-methylthiazol-5-yl. Moreover, a compound of formula I wherein $R^1$ is formyl may be treated with (p-tolylsulfonyl) methyl isocyanide (TosMIC) in the presence of potassium carbonate to afford the corresponding compound of formula I wherein $R^1$ represents oxazol-5-yl. A compound of formula I wherein $R^1$ represents hydroxymethyl may be treated with carbon tetrabromide and triphenylphosphine to afford the corresponding compound of formula I wherein $R^1$ represents bromomethyl, which may then be reacted (typically in situ) with the sodium salt of imidazole or 1H-[1,2,4]triazole to provide a compound of formula I wherein $R^1$ represents imidazol-1-ylmethyl or [1,2,4]triazol-1-ylmethyl respectively; or with the sodium salt of 1H-[1,2,3]triazole to provide a mixture of compounds of formula I wherein $R^1$ represents [1,2,3]triazol-1-ylmethyl and [1,2,3]triazol-2-ylmethyl; or with morpholine to provide a compound of formula I wherein $R^1$ represents morpholin-4-ylmethyl. A compound of formula I wherein Z is substituted with methoxy may be converted to the corresponding compound wherein Z is substituted with hydroxy by treatment with boron tribromide.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3rd edition, 1999. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human $GABA_A$ receptors containing the α2 and/or α3 and/or α5 subunit stably expressed in Ltk cells.

Reagents

Phosphate buffered saline (PBS).

Assay buffer: 10 mM $KH_2PO_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells; 10 nM for α5β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 1.8 nM; for α3β3γ2: 1.0 nM; for α5β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [$^3$H]-flumazenil from the α2 and/or α3 and/or α5 subunit of the human $GABA_A$ receptor of 100 nM or less.

EXAMPLE 1

3'-(5-Methyl-4-oxo-4,5-dihydroimidazo[4,5-c]pyridin-1-yl)biphenyl-2-carbonitrile A mixture of 2-bromobenzonitrile (9.1 g, 50 mmol), 3-aminobenzeneboronic acid monohydrate (11.6 g, 75 mmol) and tetrakis(triphenylphosphine)palladium(0) (1.73 g, 1.5 mmol) in 1,2-dimethoxyethane (50 ml) and 2 M sodium carbonate solution (25 ml) was heated at 80° C. for 20 h. After cooling to ambient temperature the reaction was partitioned between ethyl acetate (400 ml) and water (400 ml). The organics were washed with brine (400 ml), dried over anhydrous sodium sulfate, filtered and concentrated in vacuo. Purification of the residue by chromatography on silica gel, eluting with isohexane on a gradient of ethyl acetate (0–25%), gave 3'-aminobiphenyl-2-carbonitrile as a colourless oil which solidified on standing to afford a white solid (9.5 g, 98%): $\delta_H$ (400 MHz, $CDCl_3$) 3.79 (2H, br), 6.75 (1H, ddd, J 8, 3 and 1), 6.84 (1H, dd, J 3 and 3), 6.92 (1H, dd, J 8 and 3), 7.25 (1H, dd, J 8 and 8), 7.40 (1H, ddd, J 8, 8 and 1), 7.50 (1H, dd, J 8 and 1), 7.62 (1H, ddd, J 8, 8 and 1), 7.73 (1H, dd, J 8 and 1).

A suspension of 4-chloro-3-nitro-2-pyridone (1.00 g, 5.7 mmol), potassium carbonate (1.58 g, 11.5 mmol) and methyl iodide (4.07 g, 28.7 mmol) in N,N-dimethylacetamide (5 ml) were heated at 45° C. for 18 h. The mixture was allowed to cool to ambient temperature, poured into water (100 ml), layered with ethyl acetate (50 ml) and pH adjusted to 5 by the addition of 5N hydrochloric acid. The aqueous phase was extracted into ethyl acetate (2×100 ml), the combined organics were washed with water (2×100 ml) and brine (50 ml), dried over anhydrous sodium sulfate, filtered and evaporated to give a pale yellow solid. The solid was triturated with diethyl ether (20 ml), filtered and washed with diethyl ether (5 ml) and isohexane (10 ml) and left to air dry, to give 4-chloro-1-methyl-3-nitro-1H-pyridin-2-one (0.71 g, 66%) as a pale yellow solid: $\delta_H$ (360 MHz, DMSO) 3.36 (1H, dd, J 5 and 3), 3.54 (6H, s), 6.69 (2H, d, J 7), 8.09 (2H, d, J 7).

4-Chloro-1-methyl-3-nitro-1H-pyridin-2-one (0.71 g, 3.8 mmol) and 3'-aminobiphenyl-2-carbonitrile (0.73 g, 3.8 mmol) were dissolved in triethylamine (5.25 ml, 37.8 mmol) and DMSO (5 ml) and heated at 90° C. for 18 h. The mixture was allowed to cool to ambient temperature then poured onto water (150 ml). The aqueous phase was extracted with ethyl acetate (2×150 ml), the combined organics were washed with water (3×75 ml) and brine (50 ml), dried over anhydrous sodium sulfate, filtered and evaporated to give a brown solid. The solid was triturated with diethyl ether (20 ml), filtered and left to air dry, to give 3'-(1-methyl-3-nitro-2-oxo-1,2-dihydropyridin-4-ylamino)biphenyl-2-carbonitrile (1.28 g, 98%) as a brown solid: δ (400 MHz, CDCl$_3$) 3.50 (3H, s), 6.24 (1H, d, J 8), 7.26 (1H, d, J 8), 7.34 (1H, d, J 8), 7.48 (2H, dd, J 4 and 2), 7.51–7.59 (2H, m), 7.60 (1H, t, J 8), 7.68–7.72 (1H, m), 7.81 (1H, dd, J 8 and 1), 10.47 (1H, s).

3'-(1-Methyl-3-nitro-2-oxo-1,2-dihydropyridin-4-ylamino)biphenyl-2-carbonitrile (0.11 g, 0.32 mmol) was suspended in ethyl acetate (10 ml) and ethanol (10 ml), platinum oxide (7.3 mg, 0.03 mmol) added and the mixture hydrogenated at 45 psi on a Parr hydrogenator for 2 h. The catalyst was filtered off through a glass fibre filter paper and the filtrate evaporated to give 3'-(3-amino-1-methyl-2-oxo-1,2-dihydropyridin-4-ylamino)biphenyl-2-carbonitrile as an orange oil. The oil was dissolved in formic acid (4 ml) and heated at 95° C. for 24 h. The mixture was allowed to cool to ambient temperature and evaporated. The residue was made basic by the addition of concentrated ammonia solution, then diluted with water (100 ml) and extracted with dichloromethane (2×100 ml). The combined organic layer was washed with brine (50 ml), dried over anhydrous sodium sulfate, filtered and evaporated to give a brown oil. The oil was purified by flash column chromatography on silica eluting with dichloromethane (+1% concentrated ammonia) on a gradient of methanol (2–4%). Collecting appropriate fractions, followed by trituration with diethyl ether (5 ml), gave 3'-(5-methyl-4-oxo-4,5-dihydroimidazo[4,5-c]pyridin-1-yl)biphenyl-2-carbonitrile (64 mg, 61%) as a white solid: δ$_H$ (400 MHz, CDCl$_3$) 3.69 (3H, s), 6.66 (1H, d, J 7), 7.24 (2H, m), 7.52–7.58 (2H, m), 7.65–7.67 (2H, m), 7.69–7.74 (2H, m), 7.84 (1H, dd, J 8 and 1), 7.99 (1H, s); m/z (ES$^+$) 327 (M$^+$+H).

EXAMPLE 2

1-[4-Fluoro-3-(5-fluoropyridin-3-yl)phenyl]-5-methyl-1,5-dihydroimidazo[4,5-c]pyridin-4-one A solution of 5-fluoropyridin-3-ol (1.70 g, 15.0 mmol) in dry pyridine (10 ml) at 0° C. was treated with trifluoromethanesulfonic anhydride (4.23 g, 15 mmol). The solution was allowed to stir to room temperature over 12 h under nitrogen. The resulting solution was diluted with water (10 ml) and then extracted with ethyl acetate (50 ml). The organic layer was washed with 1N citric acid (2×50 ml) followed by a brine wash (50 ml). The organic layer was dried over anhydrous magnesium sulfate, filtered and evaporated to dryness. The crude product was filtered through a plug of silica gel, eluting with isohexane containing 10% ether, and concentrated to give trifluoromethanesulfonic acid 5-fluoropyridin-3-yl ester as a clear oil (3.10 g, 84%), which was used without further purification: δ$_H$ (360 MHz, d$_6$-DMSO) 8.36 (1H, m), 8.76 (1H, d, J 3), 8.83 (1H, d, J 3).

A mixture of trifluoromethanesulfonic acid 5-fluoropyridin-3-yl ester (3.67 g, 15.0 mmol), potassium acetate (2.94 g, 30.0 mmol), bis(pinacolato)diboron (4.18 g, 17.0 mmol) and dichloro[1,1'-bis(diphenylphosphino) ferrocene]palladium(II) dichloromethane (0.37 g, 0.45 mmol) in 1,4-dioxane (45 ml containing 1% dimethylsulfoxide) was degassed with nitrogen for 1 h then heated at 90° C. for 14 h. The reaction was cooled to ambient temperature and then concentrated in vacuo. The residue was stirred with 2N sodium hydroxide (300 ml) for 10 min then filtered. The filtrate was extracted with diethyl ether (2×200 ml) and the organics discarded. The aqueous component was cooled to 0° C. then treated with 36% hydrochloric acid added dropwise over 15 min until pH 5. The resulting precipitate was allowed to stand at 0° C. for 2 h then filtered and washed with ice-cold water. The sand-coloured solid was dried under vacuum (300 mmHg) over phosphorus pentoxide to afford 3-fluoro-5-(4,4,5,5-tetramethyl-[1,3,2]dioxaborolan-2-yl)pyridine as a yellow oil (3.0 g, 90%): δ$_H$ (400 MHz, CDCl$_3$) 1.25 (12H, s), 7.75 (1H, dd, J 5 and 1), 8.52 (1H, d, J 3), 8.74 (1H, s).

4-Chloro-1-methyl-3-nitro-1H-pyridin-2-one was coupled to 3-bromo-4-fluorophenylamine, in the same way as in Example 1, to give 4-(3-bromo-4-fluorophenylamino)-1-methyl-3-nitro-1H-pyridin-2-one as a beige solid (2.0 g, 40%): δ$_H$ (400 MHz, d$_6$-DMSO) 3.36 (3H, s), 5.81 (1H, d, J 8), 7.33–7.37 (1H, m), 7.45 (1H, t, J 9), 7.64–7.68 (1H, m), 7.66 (1H, s), 9.73 (1H, s).

4-(3-Bromo-4-fluorophenylamino)-1-methyl-3-nitro-1H-pyridin-2-one was reduced as in Example 1 to give 3-amino-4-(3-bromo-4-fluorophenylamino)-1-methyl-1H-pyridin-2-one as a beige solid.

3-Amino-4-(3-bromo-4-fluorophenylamino)-1-methyl-1H-pyridin-2-one was cyclised as in Example 1 to give 1-(3-bromo-4-fluorophenyl)-5-methyl-1,5-dihydroimidazo[4,5-c]pyridin-4-one as a white solid (0.91 g, 82%): δ$_H$ (400 MHz, d$_6$-DMSO) 3.53 (3H, s), 6.52 (1H, d, J 7), 7.58–7.72 (3H, m), 8.08 (1H, dd, J 6 and 3), 8.33 (1H, s).

1-(3-Bromo-4-fluorophenyl)-5-methyl-1,5-dihydroimidazo[4,5-c]pyridin-4-one was coupled to 3-fluoro-5-(4,4,5,5-tetramethyl-[1,3,2]dioxaborolan-2-yl) pyridine, in the same way as in Example 1, to give 1-[4-fluoro-3-(5-fluoropyridin-3-yl)phenyl]-5-methyl-1,5-dihydroimidazo[4,5-c]pyridin-4-one as an off-white solid (62 mg, 59%): δ$_H$ (400 MHz, d$_6$-DMSO) 3.69 (3H, s), 6.36 (1H, s), 7.23 (1H, d, J 7), 7.40–7.56 (3H, m), 7.68–7.69 (1H, m), 7.94 (1H, s), 8.57 (1H, d, J 3), 8.66 (1H, d, J 1); m/z (ES$^+$) 339 [MH$^+$].

EXAMPLE 3

5,2'-Difluoro-5'-(5-methyl-4-oxo-4,5-dihydroimidazo[4,5-c]pyridin-1-yl)-biphenyl-2-carbonitrile 2-Bromo-4-fluorobenzonitrile was converted to 4-fluoro-2-(4,4,5,5-tetramethyl-[1,3,2]dioxaborolan-2-yl) benzonitrile as described in Example 2 to give a brown solid: δ$_H$ (400 MHz, CDCl$_3$) 1.39 (12H, s), 7.18–7.23 (1H, m), 7.57 (1H, dd, J 9 and 3), 7.72 (1H, dd, J 9 and 5).

1-(3-Bromo-4-fluorophenyl)-5-methyl-1,5-dihydroimidazo[4,5-c]pyridin-4-one (0.64 g, 2.0 mmol), 4-fluoro-2-(4,4,5,5-tetramethyl-[1,3,2]dioxaborolan-2-yl) benzonitrile (0.99 g, 4.0 mmol) and potassium phosphate (0.68 g, 3.2 mmol) were placed in a flask with 1,4-dioxane (3 ml), and water (2 drops) was added. The mixture was degassed with nitrogen for 15 min before adding tris (dibenzylideneacetone)-dipalladium(0) (90 mg, 0.10 mmol) and tri-tert-butylphosphine (10% wt in hexanes, 0.20 ml, 0.10 mmol). The resulting mixture was heated at 70° C. for 16 h. The reaction mixture was allowed to cool, and then partitioned between dichloromethane (100 ml) and water (100 ml). The organic phase was washed with water (100 ml) and brine (100 ml), dried over anhydrous magnesium sulfate, filtered and pre-adsorbed onto silica. Purification by flash column chromatography on silica gel, eluting with dichloromethane on a gradient of ethanol (1–4%), gave a white solid. This solid was triturated with ethanol and filtered, yielding pure 5,2'-difluoro-5'-(5-methyl-4-oxo-4,5-dihydroimidazo[4,5-c]pyridin-1-yl)biphenyl-2-carbonitrile as a white solid (423 mg, 60%): δ$_H$ (400 MHz, d$_6$-DMSO) 3.54 (3H, s), 6.69 (1H, d, J 7), 7.59–7.62 (2H, m), 7.71 (1H, t, J 9), 7.79 (1H, dd, J 9 and 7.84–7.90 (2H, m), 8.16 (1H, dd, J 9 and 6), 8.39 (1H, s); m/z (ES$^+$) 363 [MH$^+$].

EXAMPLE 4

1-[4-Fluoro-3-(pyridin-3-yl)phenyl]-5-methyl-1,5-dihydroimidazo[4,5-c]pyridin-4-one 1-(3-Bromo-4-fluorophenyl)-5-methyl-1,5-dihydroimidazo[4,5-c]pyridin-4-one was coupled to 3-pyridylboronic acid, in the same way as in Example 1, to give 1-[4-fluoro-3-(pyridin-3-yl)phenyl]-5-methyl-1,5-dihydro-imidazo[4,5-c]pyridin-4-one as an off-white solid (50 mg, 32%): δ$_H$(400 MHz, CDCl$_3$) 3.69 (3H, s), 6.38 (1H, d, J 7), 7.22 (1H, d, J 7), 7.40–7.49 (3H, m), 7.54 (1H, dd, J 7 and 3), 7.90–7.94 (2H, m), 8.70 (1H, dd, J 5 and 2), 8.84 (1H, s); m/z (ES$^+$) 321 [MH$^+$].

EXAMPLE 5

5-Methyl-1-(2,2',3'-trifluorobiphenyl-5-yl)-1,5-dihydroimidazo[4.5-c]pyridin-4-one 1-(3-Bromo-4-fluorophenyl)-5-methyl-1,5-dihydroimidazo[4,5-c]pyridin-4-one was coupled to 2,3-difluorobenzeneboronic acid, in the same way as in Example 1, to give 5-methyl-1-(2,2',3'-trifluorobiphenyl-5-yl)-1,5-dihydroimidazo[4,5-c]pyridin-4-one as an off-white solid (32 mg, 40%): δ$_H$(400 MHz, d$_6$-DMSO) 3.54 (3H, s), 6.61 (1H, d, J 7), 7.35–7.41 (1H, m), 7.48 (1H, dd, J 8 and 7), 7.55–7.67 (3H, m), 7.77–7.81 (2H, m), 8.40 (1H, s); m/z (ES$^+$) 356 [MH$^+$].

EXAMPLE 6

4,2'-Difluoro-5'-(5-methyl-4-oxo-4,5-dihydroimidazo[4,5-c]pyridin-1-yl)biphenyl-2-carbonitrile 2-Bromo-5-fluorobenzonitrile was converted to 5-fluoro-2-(4,4,5,5-tetramethyl-[1,3,2]dioxaborolan-2-yl) benzonitrile as described in Example 2 to give a straw-coloured solid: δ$_H$ (360 MHz, CDCl$_3$) 1.38 (12H, s), 7.27 (1H, ddd, J 8, 8 and 2), 7.39 (1H, dd, J 9 and 2), 7.90 (1H, dd, J 8 and 6).

1-(3-Bromo-4-fluorophenyl)-5-methyl-1,5-dihydroimidazo[4,5-c]pyridin-4-one was coupled to 5-fluoro-2-(4,4,5,5-tetramethyl-[1,3,2]dioxaborolan-2-yl) benzonitrile, in the same way as in Example 1, to give 4,2'-difluoro-5'-(5-methyl-4-oxo-4,5-dihydroimidazo[4,5-c]pyridin-1-yl)biphenyl-2-carbonitrile as an off-white solid (360 mg, 55%): δ$_H$ (400 MHz, d$_6$-DMSO) 3.54 (3H, s), 6.67 (1H, d, J 7), 7.61 (1H, d, J 7), 7.69 (1H, t, J 9), 7.75–7.87 (4H, m), 8.09 (1H, dd, J 9 and 3), 8.38 (1H, s); m/z (ES$^+$, 363 [MH$^+$].

What is claimed is:
1. A compound of formula I:

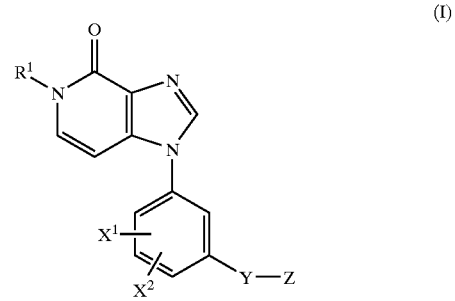

wherein:
X$^1$ represents hydrogen, halogen, C$_{1-6}$ alkyl, trifluoromethyl or C$_{1-6}$ alkoxy;
X$^2$ hydrogen or halogen;
Y represents a chemical bond, an oxygen atom, or a —NH— linkage;
Z represents a group selected from phenyl, naphthyl, pyridinyl, quinolinyl, isoquinolinyl, pyridazinyl, pyrimidinyl, pyrazinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazoly, benzimidazolyl, thiadiazolyl, triazolyl and tetrazolyl, which is unsubstituted or substituted with one or more groups selected from C$_{1-6}$ alkyl, adamantyl, phenyl, halogen, C$_{1-6}$ haloalkyl, C$_{1-6}$ aminoalkyl, trifluoromethyl, hydroxy, C$_{1-6}$ alkoxy, aryloxy, keto, C$_{1-3}$ alkylenedioxy, nitro, cyano, carboxy, C$_{2-6}$ alkoxycarbonyl, C$_{2-6}$ alkoxycarbonyl(C$_{1-6}$)alkyl, C$_{2-6}$ alkylcarbonyloxy, arylcarbonyloxy, aminocarbonyloxy, C$_{2-6}$ alkylcarbonyl, arylcarbonyl, C$_{1-6}$ alkylthio, C$_{1-6}$ alkylsulphinyl, C$_{1-6}$ alkylsulphonyl, arylsulphonyl, —NR$^v$R$^w$,—NR$^v$COR$^w$, —NR$^v$CO$_2$R$^w$, —NR$^v$SO$_2$R$^w$, —CH$_2$NR$^v$SO$_2$R$^w$, —NHCONR$^v$R$^w$, —CONR$^v$R$^w$, —SO$_2$NR$^v$R$^w$ and —CH$_2$SO$_2$NR$^v$R$^w$, in which R$^v$ and R$^w$ independently represent hydrogen, C$_{1-6}$ alkyl, phenyl or phenyl(C$_{1-6}$)alkyl;
R$^1$ represents C$_{1-6}$ alkyl, phenyl, naphthyl, pyridinyl, quinolinyl, isoquinolinyl, pyridazinyl, pyrimidinyl, pyrazinyl, furyl, benzofuryl, dibenzofuryl, thienyl, benzthienyl, pyrrolyl indolyl, pyrazolyl, indazolyl, oxazolyl, isoxazolyl, thiazolyl, isothiazolyl, imidazolyl, benzimidazolyl, thiadiazolyl, triazolyl, tetrazolyl, trifluoromethyl, —SO$_2$R$^a$, —SO$_2$NR$^a$R$^b$, —COR$^a$, or —CONR$^a$R$^b$; and
R$^a$ and R$^b$ independently represent hydrogen, C$_{1-6}$ alkyl, phenyl, naphthyl, pyridinyl, quinolinyl, isoquinolinyl, pyridazinyl, pyrimidinyl, pyrazinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, thiadiazolyl, triazolyl, tetrazolyl;
or a pharmaceutically acceptable salt thereof.
2. The compound of claim 1 wherein X$^1$ is hydrogen, fluoro, chloro, methyl, trifluoromethyl or methoxy.
3. The compound of claim 1 wherein X$^2$ is hydrogen or fluoro.
4. The compound of claim 1 wherein Z is a group selected from phenyl, pyridinyl, pyridazinyl, pyrimidinyl, pyrazinyl, furyl, thienyl, oxazolyl, isoxazolyl, thiazolyl, isothiazolyl, pyrrolyl, pyrazolyl, imidazolyl, thiadiazolyl, triazolyl and trazolyl, which is unsubstituted or substituted with one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, aminocarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, —NR$^v$R$^w$, —NR$^v$COR$^w$, —NR$^v$CO$_2$R$^w$, —NR$^v$SO$_2$R$^w$, —CH$_2$NR$^v$SO$_2$R$^w$ —NHCONR$^v$R$^w$, —CONR$^v$R$^w$, —SO$_2$NR$^v$R$^w$, and —CH$_2$SO$_2$NR$^v$R$^w$, in which R$^v$ and R$^w$ independently represent hydrogen, $C_{1-6}$ alkyl, phenyl or phenyl($C_{1-6}$)alkyl.

5. The compound of claim 1 wherein $R^1$ is $C_{1-6}$ alkyl, phenyl, naphthyl, pyridinyl, quinolinyl, isoquinolinyl, pyridazinyl, pyrimidinyl, pyrazinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, thiadiazolyl, triazolyl, tetrazolyl, trifluoromethyl, —COR$^a$ or —CO$_2$R$^a$.

6. The compound of claim 5 wherein R$^a$ is hydrogen or $C_{1-6}$ alkyl.

7. A compound which is selected from the group consisting of:

3'-(5-methyl-4-oxo-4,5-dihydroimidazo[4,5-c]pyridin-1-yl) biphenyl-2-carbonitrile;

1-[4-fluoro-3-(5-fluoropyridin-3-yl)phenyl]-5-methyl-1,5-dihydroimidazo[4,5-c]pyridin-4-one;

5,2'-difluoro-5'-(5-methyl-4-oxo-4,5-dihydroimidazo[4,5-c]pyridin-1-yl)-biphenyl-2-carbonitrile;

1-[4-fluoro-3-(pyridin-3-yl)phenyl]-5-methyl-1,5-dihydroimidazo[4,5-c]pyridin-4-one;

5-methyl-1-(2,2', 3'-trifluorobiphenyl-5-yl)-1,5-dihydroimidazo[4,5-c]pyridin-4-one;

4,2'-difluoro-5'-(5-methyl-4-oxo4,5-dihydroimidazo[4,5-c] pyridin-1-yl)biphenyl-2-carbonitrile;

or a pharmaceutically acceptable salts thereof.

8. A pharmaceutical composition comprising a compound of claim 1, or a pharmaceutically acceptable salt thereof, and a pharmaceutically acceptable excipient.

9. A method for treatment of anxiety comprising administering to patient in need thereof a therapeutically effective amount of a compound of claim 1 or a pharmaceutically acceptable salt thereof.

* * * * *